(12) United States Patent
Offenbacher et al.

(10) Patent No.: US 8,163,165 B2
(45) Date of Patent: Apr. 24, 2012

(54) GAS SENSOR WITH A MICROPOROUS ELECTROLYTE LAYER

(75) Inventors: Helmut Offenbacher, Graz (AT); Gregor Steiner, Lübeck (DE); Claudia-Gemma Muresanu, Graz (AT)

(73) Assignee: Roche Diagnostics Operations, Inc., Indianapolis, IN (US)

(*) Notice: Subject to any disclaimer, the term of this patent is extended or adjusted under 35 U.S.C. 154(b) by 64 days.

(21) Appl. No.: 12/837,733

(22) Filed: Jul. 16, 2010

(65) Prior Publication Data
US 2011/0079523 A1   Apr. 7, 2011

Related U.S. Application Data

(63) Continuation of application No. PCT/EP2009/000273, filed on Jan. 16, 2009.

(30) Foreign Application Priority Data

Jan. 18, 2008   (EP) .................................. 08000943

(51) Int. Cl.
*G01N 27/404* (2006.01)
(52) U.S. Cl. ......... 205/792; 204/431; 205/783; 205/775
(58) Field of Classification Search ............... 205/778.5, 205/775, 779, 782–783, 785.5; 204/431, 204/400, 430, 432
See application file for complete search history.

(56) References Cited

U.S. PATENT DOCUMENTS

| | | | |
|---|---|---|---|
| 5,387,329 A | 2/1995 | Foos et al. | |
| 7,232,511 B1 * | 6/2007 | Venkatasetty | 204/403.01 |
| 2004/0033414 A1 | 2/2004 | Rohrl | |
| 2006/0021873 A1 | 2/2006 | Mett | |
| 2006/0293169 A1 | 12/2006 | Srinivasan et al. | |
| 2008/0209876 A1 * | 9/2008 | Miller | 55/522 |
| 2010/0252428 A1 * | 10/2010 | Lauks et al. | 204/400 |

FOREIGN PATENT DOCUMENTS

| | | |
|---|---|---|
| EP | 0097554 A2 | 1/1984 |
| EP | 0299780 A2 | 1/1989 |
| EP | 0805973 B1 | 11/1997 |
| GB | 2308193 A | 6/1997 |

* cited by examiner

*Primary Examiner* — Alex Noguerola
(74) *Attorney, Agent, or Firm* — Roche Diagnostics Operations, Inc.

(57) ABSTRACT

The present invention relates to electrochemical sensors for determining gaseous analytes in an aqueous measuring medium, to a process for producing such sensors, and to a process for determining gaseous analytes dissolved in an aqueous measuring medium using the electrochemical sensors. The electrolyte layer of the sensors comprises at least one particulate material and at least one binder which together form a porous, non-swellable framework structure, wherein the pores in this framework structure are configured to absorb a liquid electrolyte or contain the liquid electrolyte.

43 Claims, 3 Drawing Sheets

GAS SENSOR WITH A MICROPOROUS ELECTROLYTE LAYER

BACKGROUND OF THE INVENTION

The present invention relates to electrochemical sensors for determining gaseous analytes dissolved in an aqueous measuring medium, to a method for the manufacture thereof, and also to a method for determining gaseous analytes dissolved in an aqueous measuring medium using the electrochemical sensors. The invention relates in particular to the reaction space of the electrochemical sensors, which is spatially separated from the aqueous measuring medium by a gas-permeable and ion-impermeable cover layer.

Measuring systems for analysing body fluids are important components of clinically relevant analysis methods. A particular focus of this is rapid and precise measurement of analytes, allowing what are known as point-of-care parameters to be determined. Point-of-care tests have the advantage that the results are available after just a short time, as on the one hand there is no need to transport the samples to a specialist laboratory and on the other hand it is not necessary to take account of the laboratory timescales. Point-of-care tests are carried out mainly in intensive care units and in anaesthesia, but also in outpatient clinics. These "emergency parameters" include the blood gas values ($pCO_2$, $pO_2$), the pH, electrolyte values (for example, $Na^+$, $K^+$, $Ca^{2+}$, $Cl^-$) and also certain metabolite values.

Test strips or else medical analysers with multiuse sensors can for example be used to carry out point-of-care tests of this type, thus reducing the manual implementation effort to a minimum. Measuring apparatuses for a point-of-care use are generally almost fully automated and require, from the preparation of the samples up to the result of the test, only a small number of simple interventions on the part of the user. They can be embodied both for one-off and for repeated measurement of the parameters to be determined.

Electrochemical sensors have proven particularly suitable for measuring gaseous analytes, such as for example oxygen or carbon dioxide dissolved in whole blood or other aqueous media. Electrochemical sensors allow an analyte to be measured by means of two or more electrodes, at least one of the electrodes being the working electrode at which the analyte to be determined is electrochemically altered (for example, oxidised or reduced).

The measurement of oxygen or the partial pressure ($pO_2$) thereof in an aqueous measuring medium can for example be carried out using amperometric sensors comprising at least one, working electrode and at least one counter electrode. In Clark-type electrodes, a gas-permeable and largely ion and liquid-impermeable membrane generally spatially separates the sample space from the inner electrolyte space. The inner electrolyte space is filled with an electrolyte solution containing a working electrode and a counter electrode.

The measurement of carbon dioxide or the partial pressure ($pCO_2$) thereof in liquids or gases can for example be carried out using potentiometric sensors comprising at least one measuring electrode and at least one reference electrode. In Severinghaus-type electrodes, the measurement of the $CO_2$ partial pressure is reduced to a pH measurement. This generally requires a reaction space which is spatially separated from the aqueous measuring medium by a gas-permeable and largely ion-impermeable membrane. The pH, which is determined by the respective $pCO_2$ value of the sample to be measured, is measured in this reaction space. At a predefined temperature and concentration of the buffer solution in the reaction space (inner electrolyte), the pH of the reaction space is dependent exclusively on the $CO_2$ partial pressure of the sample. The pH can be detected in a broad range of ways, for example potentiometrically via an electrochemical measuring chain using ion-selective glass electrodes or ion-sensitive or ion-selective field effect transistors (ISFETs), pH-sensitive solid-state systems (for example, noble metal/noble metal oxide systems), redox systems (quinhydrone electrode), etc.

An important criterion in the provision of electrochemical sensors is the service life thereof. There is a need to achieve in this regard both a long storage life before the sensor is put into operation and a long in-use service life. In order to ensure a long storage life, the electrodes located in electrochemical sensors should be stored dry, i.e., substantially without water, and not be brought into contact with the liquid inner electrolyte until just before the sensor is put into operation. In order to achieve an in-use service life of at least 500 measurements or 3 to 4 weeks, the various layers of the sensor must also be compatible with one another. It is imperative that they should not become detached from one another or form cracks, for example as a result of swelling.

A further important criterion in the provision of electrochemical sensors for point-of-care tests is the dimensions thereof. Small quantities of samples (for example, 100 µl or less) are generally available in order to determine emergency parameters. If a large number of parameters are to be determined using small quantities of samples, the individual electrodes must be as small as possible and positioned as close together as possible.

EP 0 805 973 B1 discloses a device and also a method for measuring the concentration of gases in a sample. The device used is an electrochemical sensor comprising a working electrode, a counter or reference electrode, an electrolyte layer and a gas-permeable membrane, the electrolyte layer consisting of a photoformed proteinaceous gelatin. In order to avoid premature contamination of the negatively polarised working electrode (cathode), which is made of gold, by positively charged silver ions originating from the counter electrode (anode), which is made of silver, the distance between the two electrodes, which are electrically contacted by a layer of gelatin, must be at least 1 mm.

U.S. Pat. No. 5,387,329 describes a planar electrochemical oxygen sensor in which a swellable polymer, the swell value of which is less than two times its dry volume, is used as a hygroscopic electrolyte and forms in this case a hydrophilic electrolyte layer which is permeable by water and cations. A swellable polymer which is preferred within this document is Nafion®, a sulphonated tetrafluoroethylene polymer, the lithium-charged sulphonate groups of which impart ionomeric properties to the polymer and cause lithium ions to be exchanged for silver ions. In an amperometric oxygen sensor with a silver counter electrode, this reduces the effective speed of migration of the silver ions toward the working electrode.

The electrolyte layers used in EP 0 805 973 B1 and U.S. Pat. No. 5,387,329 have a number of drawbacks. Thus, for example, the production of very thin layers (approx. 1 µm) of swellable polymers (for example the proteinaceous gelatins which are photoformed in EP 0 805 973 B1) is very expensive.

Furthermore, in the case of very thin layers and very low electrolyte volumes, the silver ions released during operation of an oxygen sensor soon lead to interfering signals. On the other hand, if thicker swelling layers (approx. 10-50 µm) are used in a multilayered construction, the formation of leaks in the layer construction is facilitated. This makes it difficult to achieve the desired longevity of the sensor.

In addition, a major drawback of thin, water-containing polymer layers is the fact that, after an electric field is applied between the two electrodes, interfering silver ions migrate on a direct path through the polymer and thus reach and contaminate the working electrode after a relatively short operating period.

SUMMARY OF THE INVENTION

It is against the above background that the present invention provides certain unobvious advantages and advancements over the prior art. In particular, the inventors have recognized a need for improvements in electrochemical sensors for determining a gaseous analyte.

Although the present invention is not limited to specific advantages or functionality, it is noted that the present invention provides for the ability to store the sensor for a long period of time without thereby losing activity and, in addition, extend the in-use service life of the sensor after it has been put into operation. Furthermore, manufacturing of sensors in accordance with the present invention can be done more simply and cost-effectively.

In accordance with one embodiment of the present invention, an electrochemical sensor for determining a gaseous analyte dissolved in an aqueous measuring medium is provided, comprising: (a) a working electrode and a counter electrode, (b) an electrolyte layer located between the working electrode and the counter electrode, and (c) a gas-permeable cover layer configured to spatially separate the working electrode, the counter electrode and the electrolyte layer from the aqueous measuring medium. The electrolyte layer comprises at least one particulate material and at least one binder which together form a porous, non-swellable framework structure. The pores of the non-swellable framework structure are configured to absorb a liquid electrolyte or contain the liquid electrolyte.

In accordance with another embodiment of the present invention, a method for manufacturing an electrochemical sensor according to the invention is provided and comprises: (a) providing at least one particulate material; (b) mixing the particulate material with at least one binder and, if appropriate, further substances; (c) processing the mixture obtained in step (b) into a paste; (d) applying the paste obtained in step (c) to a support; (e) hardening the paste applied to the support to form, a porous, non-swellable framework structure; and (f) producing an electrochemical sensor containing the porous, non-swellable framework structure obtained in step (e) as an electrolyte layer, and also a working electrode, a counter electrode and a gas-permeable cover layer.

In accordance with yet another embodiment of the present invention, a method for determining a gaseous analyte dissolved in an aqueous measuring medium is provided, comprising: (a) contacting the aqueous measuring medium with an electrochemical sensor according to the invention, and (b) determining the gaseous analyte dissolved in the aqueous measuring medium by measuring a signal generated by the electrochemical sensor.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1A:
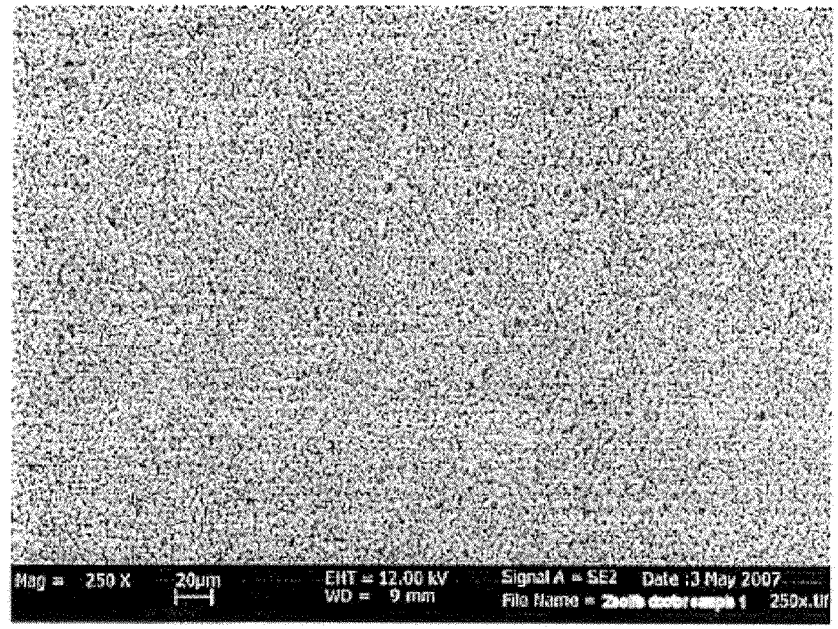
FIG. 1a and FIG. 1b are electron micrographs of the porous electrolyte layer in an electrochemical sensor according to an embodiment of the present invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

The expression "determining a gaseous analyte dissolved in an aqueous medium", such as it is used within this application, includes both determining the presence or the concentration of the dissolved gas component in the aqueous medium and determining the gas partial pressure of the dissolved gas component in the aqueous medium.

According to the invention, the pores of the non-swellable framework structure are located between the particles of the at least one particulate material. Compared to a pure polymer layer or gelatin or gel layer, the labyrinth of pores formed in this way increases the distance that the ions moving between the electrodes have to cover, and thus increases the service life of the sensor.

Particulate materials which are used in the electrochemical sensors of the present invention may be inorganic or organic in nature and comprise in particular dense inorganic materials or dense (unplasticised) organic polymers. Suitable inorganic particulate materials include controlled porous glass (CPG), silica gels, silicates and alumosilicates (also referred to as aluminosilicates), which are selected mainly from the group consisting of tectosilicates and phyllosilicates. Organic polymers which can be used in accordance with the invention as particulate material include, for example, but are not limited to, microparticles of polystyrene, polyamide, polyvinyl chloride, polyvinylidene chloride, poly(meth)acrylate, polyacrylonitrile and also copolymers thereof.

The use of a naturally occurring or synthetic alumosilicate, more typically a synthetic alumosilicate, as particulate material has proven advantageous within the invention. The term "synthetic alumosilicate", as it is used within the present invention, includes both fully synthetic alumosilicates and alumosilicates obtained by artificial alteration (for example, chemically) of a naturally occurring alumosilicate. Examples of naturally occurring or synthetic alumosilicates include, but are not limited to, feldspars, mica, mullite, sillimanite and zeolites.

In a variant of the electrochemical sensor according to the invention, the particulate material has channels, in particular channels having a diameter of between about 0.1 nm and about 10 nm, and optionally ion exchanger groups. In another embodiment, the particulate material is a zeolite, for example faujasite, chabazite, mordenite or natrolite, containing polyhedrons, layers or chains of corner-linked $[(Al,Si)O_4]$ tetrahedrons which form an anionic three-dimensional network traversed by channels. Depending on the type of zeolite, the channels have a diameter of from about 0.5 nm to about 5.0 nm, typically from about 0.7 nm to about 2.0 nm, and contain ion exchanger groups, in particular cation exchanger groups, at their inner and outer surfaces. The use of zeolites with an inner channel structure and ion exchanger groups has proven particularly advantageous, in particular in Clark-type amperometric electrodes. In yet another typical embodiment, the sensor according to the invention comprises faujasite, more typically faujasite-Na, as the particulate material.

As a consequence of its channel-containing configuration, zeolites have a large inner surface which can enter into contact with a liquid electrolyte. As, on the other hand, suitably sized ions contained in the electrolyte liquid can migrate through the channels of the zeolite, the quantity of undesirable ions can be reduced. Thus, in electrochemical sensors containing silver-containing counter electrodes, there is the particular problem that when the sensor is put into operation, silver ions are released from the counter electrode, migrate towards the working electrode and upon passivating the working electrode are deposited thereon as elemental silver. Similar processes also occur in other metals used as electrode materials, for example lead, which, on contact with the electrolyte liquid, can release lead ions which can likewise act as interfering cations. The use of an electrochemical sensor according to the present invention, the electrolyte layer of which typically comprises at least one zeolite, allows the effective distance between the counter electrode and working electrode to be increased and the risk of rapid passivation of the working electrode thus to be reduced, resulting in an improved service life of the sensor.

On the other hand, the anionic framework structure of zeolites also allows them to act as ion exchangers. Thus, for example, silver ions which are released from the counter electrode and migrate toward the working electrode can be absorbed by zeolites and exchanged for suitable, less critical cations, for example sodium ions, as a result of which the quantity of free silver ions in the electrolyte is reduced and passivation of the working electrode can be counteracted; this also leads to an improved service life of the sensor.

The size of the particles of the particulate material can be varied as required in any given case. Within the present invention, the particles of the particulate material conventionally have an average particle diameter of from about 0.1 μm to about 10 μm, an average particle diameter of from about 1.0 μm to about 5.0 μm being typical. In any case, the particle size of the porous material should always be less than the layer thickness of the electrolyte layer, which is in the range of from about 5 μm to about 30 μm, and typically in the range of from about 10 μm to about 20 μm.

In addition to the particulate material, the electrolyte layer comprises at least one binder as a further component. Typically, the binder is an organic binder, for example a crosslinked or uncrosslinked, linear or branched organic polymer. More typically, the organic binder contained in the electrolyte layer comprises any desired crosslinked or uncrosslinked synthetic polymer which can be selected from the group consisting of a phenolic resin, an epoxy resin, a vinyl resin, a PVC copolymer, a two-component epoxy resin, a polyurethane resin system and a UV-curable polyacrylate monomer mixture. The crosslinked or uncrosslinked synthetic polymer used can be a phenolic resin, in particular a crosslinked phenolic resin.

The amount of the non-swellable binder is such that the binder connects the particles of the inorganic or organic particulate material to form a porous, non-swellable framework structure. This means that the binder does not completely fill out the intermediate spaces between the particles of the particulate material, thus forming a non-swellable framework structure having pores with a diameter of from about 500 nm to about 5 μm, typically from about 1 μm to about 3 μm. According to an embodiment of the invention, the porous, non-swellable framework structure causes a relative absorption of liquid of from about 20% by weight to about 50% by weight, typically from about 26% by weight to about 44% by weight, based on the dry weight of the porous, non-swellable framework structure.

Figure 1B:
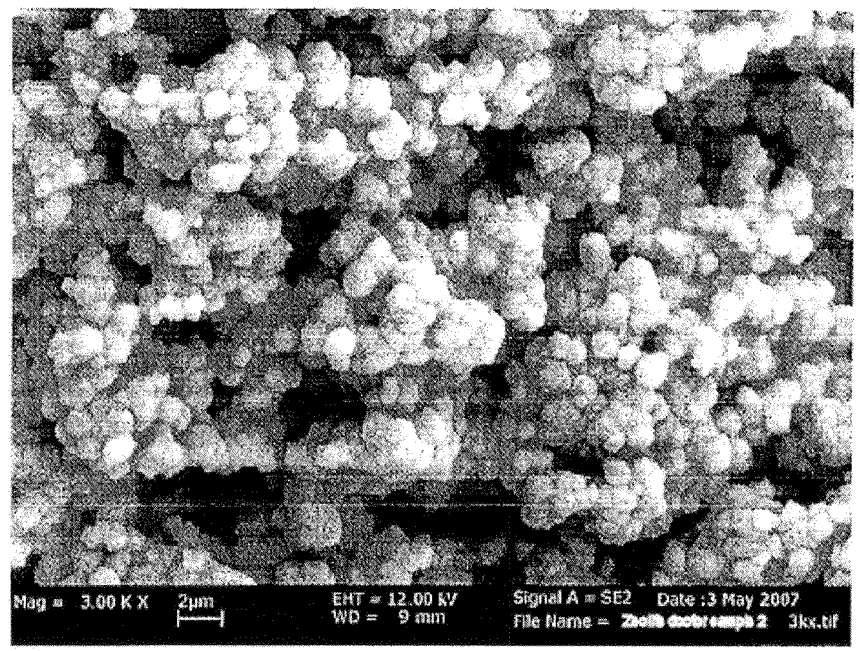
Figure 2:
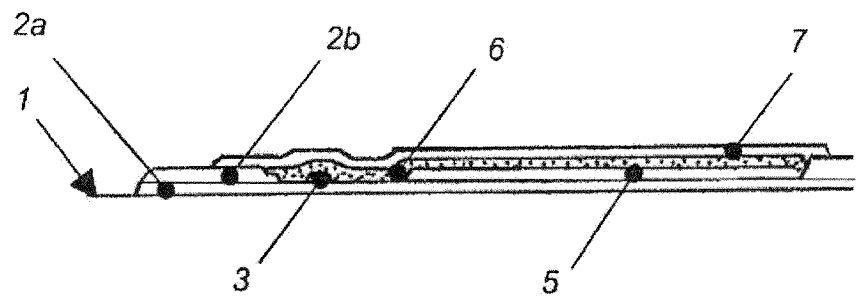
FIG. 2 is a section through the channel region in an electrochemical $pO_2$ sensor according to an embodiment of the present invention. The support (1) used is a plate made of an Al/Mg alloy, which is coated with a thin layer of polycarbonate and to which a gas barrier layer (2a) is attached that serves, for its part, to minimise or completely prevent the diffusion of gases into or out of the polycarbonate layer. An insulating layer (2b), which is provided to prevent interference potentials/currents on liquid contact, is applied to the gas barrier layer (2a). A window, which is closed with a gas-permeable cover layer (7), is formed in the measuring region. The electrochemical $pO_2$ sensor per se consists of the working electrode (3), the counter electrode (5), the porous electrolyte layer (6), which extends along the measuring channel and completely covers the active faces of both the working electrode (3) and the counter electrode (5), and also the gas-permeable cover layer (7), which in turn completely covers the porous electrolyte layer (6).
Figure 3A:
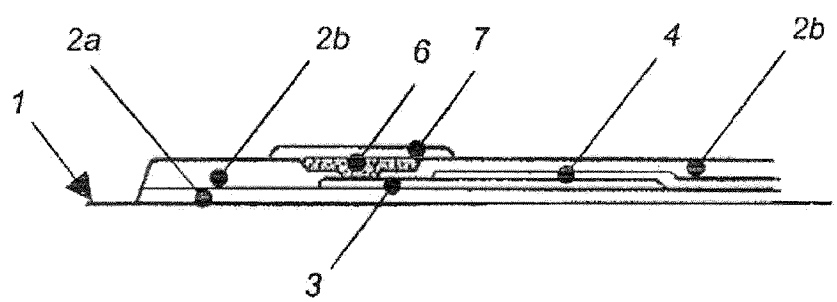
FIG. 3a is a longitudinal section through the working electrode in an electrochemical $pO_2$ sensor according to an embodiment of the present invention. The working electrode (3) is typically made of a gold-based composite material which furthermore contains a polymeric component. The working electrode discharge line (4), one end of which is in planar contact with the working electrode (3) and a second end of which forms an open contact for an electrical plug-in connection, can for example be made of a thin, elongated, silver-based composite material. The remaining reference numerals each have the meaning indicated in FIG. 2.
Figure 3B:
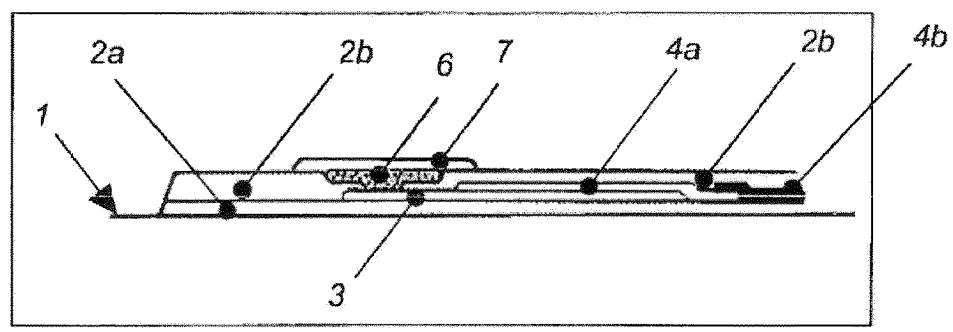
FIG. 3b is a longitudinal section through the working electrode with an alternative silver bridge layer and silver/silver chloride conductor in an electrochemical $pO_2$ sensor according to an embodiment of the present invention. In this case, the only modification from FIG. 3a is a bridge layer (2a) which transforms outside the measuring region into a silver/silver chloride conductor (4b). The conductor (4b) can be produced, for example, by means of screen printing from a corresponding screen printing paste. The remaining reference numerals each have the meaning indicated in FIG. 2.
Figure 4:
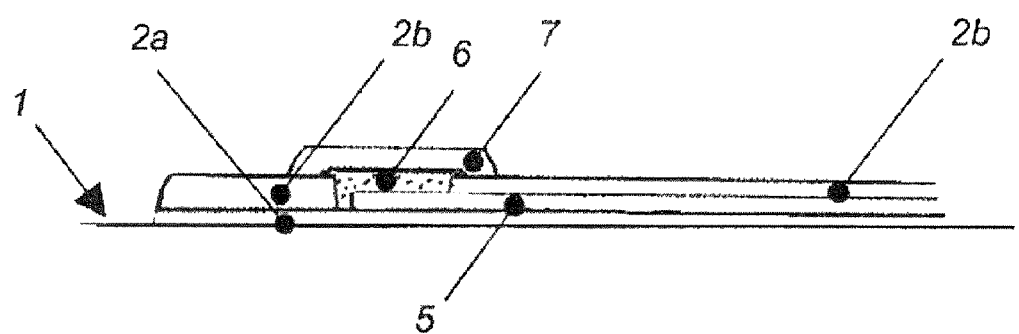
FIG. 4 is a longitudinal section through the counter electrode in an electrochemical $O_2$ sensor according to an embodiment of the present invention. The counter electrode (5), which can be produced, for example, by means of screen printing, is typically made of a silver-based composite material which further contains a polymeric component. The remaining reference numerals each have the meaning indicated in FIG. 2.
Figure 5:
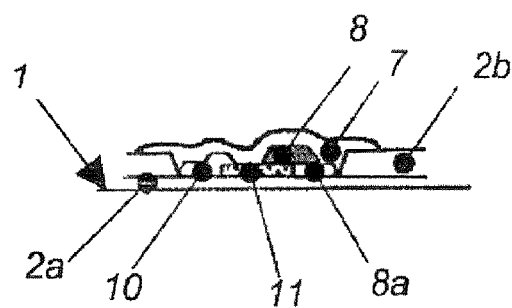
FIG. 5 is a section through the channel region in an electrochemical $CO_2$ sensor according to an embodiment of the present invention. The electrochemical $CO_2$ sensor per se consists of the working electrode (8) (pH-sensitive measuring electrode), a bridge layer (8a), the counter electrode (reference electrode) (10), a porous electrolyte layer (11) and also a gas-permeable cover layer (7). The working or pH electrode (8), which can be generated, for example, by means of screen printing, is typically made of a ruthenium oxide-based composite material which further contains a polymeric component. This layer is electrically conducted from the direct measuring region by means of a bridge layer (8a) generated, for example, from a graphite paste. The counter electrode (10), which is constructed in a layer-like manner, is generated in particular by means of screen printing and is typically made of a silver/silver chloride-based composite material. The remaining reference numerals each have the meaning indicated in FIG. 2.

The required amounts of binder may vary depending on the type and amount of the particulate material used as well as the desired pore size, and can be adapted to the requirements of any given situation by a person skilled in the art. FIGS. 1a and 1b each show electron micrographs of the electrolyte layer of a sensor according to an embodiment of the invention, in which layer particles of a particulate material are connected using a binder to form a porous, non-swellable framework structure. The porous, non-swellable framework structure displays a uniform distribution of the pores and consists of units which are generally about 1 to 3 particles wide and connected in a chain-like manner.

According to yet another embodiment of the invention, the electrolyte layer can further comprise, in addition to the at least one particulate material and the at least one binder, one or more auxiliaries. Auxiliaries which can be used for this purpose include in particular synthetic cellulose derivatives, for example alkyl celluloses, the term "alkyl" representing a straight-chain or branched hydrocarbon radical containing 1 to 6 carbon atoms. Typical alkyl celluloses in the sense of the present invention are selected from the group consisting of methyl cellulose, ethyl cellulose, propyl cellulose, ethyl methyl cellulose and propyl methyl cellulose. The wetting ability of the surface of the structure with the liquid electrolyte can be improved by adding small amounts of these alkyl celluloses. Further suitable auxiliaries include for example antifoaming agents.

The liquid electrolyte, which ensures a conductive electrolyte connection between the working electrode and the counter electrode in the electrochemical sensor according to the invention, may be any desired electrolyte, for example a water-based electrolyte which, on the application of a voltage, causes charge carriers to be transported as a result of directed movement of ions. Within the present invention, it is typical for the liquid electrolyte to contain an alkali metal chloride and a pH buffer system.

Sodium and/or potassium chloride can in particular be used as the alkali metal chloride which serves in an electrochemical sensor according to the present invention as a conductive salt component of the liquid electrolyte. The use of sodium and/or potassium chloride as the main component of the electrolyte has the advantage that the silver ions which are released from the counter electrode on use of silver-containing counter electrodes are additionally prevented, as a consequence of the precipitation of silver chloride, from migrating towards the working electrode, as a result of which the deposition of elemental silver on the working electrode can be reduced.

pH buffer systems which can be used for the liquid electrolyte solution include any desired buffer systems which are known to those of ordinary skill in this art field and serve to stabilise the pH in a liquid medium. Exemplary pH buffer systems include, but are not limited to, bicarbonate buffer, phosphate buffer and the like.

In another typical embodiment, the liquid electrolyte further comprises, in addition to the alkali metal chloride and the pH buffer system, at least one water-soluble polymer. The water-soluble polymer used may be any desired polymer which causes, when introduced into the liquid electrolyte solution described hereinbefore, an increase in the viscosity of the liquid and can thus also help to reduce the speed of migration of released ions, for example released silver ions. Water-soluble polymers which can be used within the present invention are, for example, polyethylene glycol, polyvinylpyrrolidone and alkyl polyglycosides, the electrolyte liquid containing typically polyethylene glycol and/or polyvinylpyrrolidone as the water-soluble polymer. An electrolyte liquid of this type can be used particularly advantageously in sensors for determining oxygen.

In an alternative embodiment, the electrolyte liquid can additionally comprise, in addition to the alkali metal chloride and the pH buffer system, an enzyme which speeds up a desired reaction, for example the hydration of a predetermined substrate. An enzyme which is typical within the present invention is carbonic anhydrase, which in the presence of water catalyses the hydration of carbon dioxide into hydrogen carbonate. An electrolyte of this type is suitable in particular for Severinghaus-type electrodes, in which the determination of carbon dioxide is based on a pH measurement of the inner electrolyte.

Within the present invention, it is furthermore typical for the electrolyte layer to comprise the non-volatile constituents of the liquid electrolyte before the electrochemical sensor is put into operation. For this purpose, a liquid containing these constituents, typically the liquid electrolyte, can be introduced, for example by dropping-on, into the pores of the non-swellable framework structure and stored, after removal of an electrolyte liquid supernatant, for example by dabbing-off, for a period of several hours, for example for a period of 48 hours or more, at a temperature of >25° C., for example at a temperature of 65° C., in order to allow the volatile constituents of the liquid electrolyte to evaporate. In this way, it is possible to ensure that, after the drying step, the electrolyte layer of the electrochemical sensor contains the non-volatile constituents of the electrolyte, for example alkali metal chlorides, constituents of the pH buffer systems and also further substances comprising inter alia water-soluble polymers or enzymes.

Alternatively, a liquid containing the non-volatile electrolyte constituents can be added, even before the porous, non-swellable framework structure is formed, to a mixture which contains the at least one particulate material, the at least one binder and if appropriate further substances and is for example in the form of a paste. The mixture obtained in this way can subsequently be hardened, thus forming a porous, non-swellable framework structure, the pores of which contain the non-volatile constituents of the liquid electrolyte. This procedure has the advantage over the above-described method, i.e., over an introduction of the liquid electrolyte into the pores of a pre-existing framework structure, that the various constituents of the liquid electrolyte can be introduced more easily, more homogeneously and more reproducibly into the porous, non-swellable framework structure of the sensor according to the invention.

The gas-permeable cover layer allows the analyte, which is gaseous (under normal conditions), to infiltrate the electrochemical sensor, although it is in particular intended to prevent ions and/or non-volatile constituents of the aqueous measuring medium from entering. In a typical embodiment, the gas-permeable cover layer is therefore impermeable to ions and non-volatile constituents of the aqueous measuring medium.

The gas-permeable cover layer can be made of any desired material which can be considered for purposes of this type. Typically, the gas-permeable cover layer comprises at least one polymeric material, siloxanes, polysulphones and/or polytetrafluoroethylene having proven particularly advantageous. The siloxane used, which is beneficial within the present invention, may for example be an oxime-crosslinking silicone rubber such as is commercially available under the trade name DELO-GUM® SI480 (from DELO, Germany). Suitable polysulphones include in particular polysulphones having relatively long alkyl chains, for example $C_{16}$ alkyl chains. A product of this type is known under the trade name BIOBLAND (from ANATRACE, USA).

The gas-permeable cover layer can be produced in different ways. A typical method consists of the use of prefabricated cover layers which are attached to the electrochemical sensor. The membrane can be fixed to the sensor in this regard by means of any desired processes, wherein adhesive bonding or laser welding are to be regarded as typical.

Alternatively, it is possible to produce the gas-permeable cover membrane in situ in that a solution of a suitable gas-permeable polymer or prepolymer is applied to the electrochemical sensor and subsequently dried. The polymer is applied to the electrochemical sensor typically by spraying-on, dip coating, dispersing or screen printing a typically diluted solution of the polymer or prepolymer, although the application is not limited to these methods. The solvent used is typically an organic solvent, in particular an organic solvent having a boiling point of $\leq 100°$ C., wherein a person skilled in the art can in principle select a suitable solvent depending on the properties of the polymer or prepolymer used and/or the application process.

The gas-permeable cover layers which are obtained in this way and used in an electrochemical sensor according to the present invention conventionally have a thickness of from about 5.0 µm to about 30 µm, typically from about 8.0 µm to about 15 µm.

The working electrode and counter electrode of the electrochemical sensor according to the invention can be made of any desired material which is suitable for the purposes of the present invention. The working electrode is typically made of a gold or ruthenium oxide-based composite material, a gold-based composite material being suitable in particular for sensors for amperometrically determining oxygen, and a ruthenium oxide-based composite material being suitable in particular for sensors for potentiometrically determining carbon dioxide by means of a pH electrode in accordance with the Severinghaus principle. Conversely, the counter electrode of a sensor according to the invention is typically made of a silver or silver/silver chloride-based composite material. In this regard, a silver-based composite material has proven advantageous in particular for counter electrodes in sensors for determining oxygen, whereas a silver/silver chloride-based composite material can typically be used for counter electrodes in sensors for determining carbon dioxide. The terms "working electrode" and "measuring electrode" or the terms "counter electrode" and "reference electrode", such as are commonly used in the present art field, in each case predominantly for either amperometric electrodes or potentiometric electrodes, are used synonymously within this application.

The conductive electrode material, which, to produce the electrode matrix, can be provided for example in the form of a paste, comprises in addition to the metal or metal oxide, both in the case of the working electrode or measuring electrode and in the case of the counter electrode or reference electrode, typically a non-conductive polymeric binder, vinyl resins being preferred.

Typically, the electrochemical sensor according to the invention is configured for a multiple measurement of the analyte to be determined. This is desirable in particular in applications in which a sensor is to be used to measure a large number of samples or in which a constant, i.e., continuous or discontinuous, monitoring of the presence and/or of the amount of an analyte is to be carried out over a relatively long period of time, for example 1 day or longer, in particular 1 week or longer. In a typical embodiment, the invention accordingly provides for the electrochemical sensor to be embodied as a measuring cell, through which a sample liquid containing the gaseous analyte is passed and which is for example part of an analyser.

The electrochemical sensor according to the invention can be used for determining a gaseous analyte dissolved in an aqueous measuring medium which can originate from any desired source. In one typical embodiment, the electrochemical sensor is configured to determine a gaseous analyte which is dissolved in a body fluid comprising, but not limited to, whole blood, plasma, serum, lymph fluid, bile fluid, cerebrospinal fluid, extracellular tissue fluid, urine, and also gland secretions, for example saliva or sweat, whole blood, plasma and serum being regarded as particularly preferred. The gaseous analyte, which is to be determined qualitatively and/or quantitatively, is typically oxygen or carbon dioxide.

For the purposes of manufacturing the electrochemical sensors according to the invention, at least one inorganic or organic particulate material is mixed with at least one inorganic or organic binder, which are each defined as stated hereinbefore, and, if appropriate, further substances and processed to form a paste. After the application of the paste to a support and subsequent hardening of the paste, a porous, non-swellable framework structure is formed that can be used as an electrolyte layer in an electrochemical sensor according to the present invention. The electrochemical sensor contains, in addition to the porous electrolyte layer, a working electrode, a counter electrode and a gas-permeable cover layer.

For carrying out the method described hereinbefore, the paste can, for example, be applied to a support by means of screen printing or doctoring processes. Thus, in one embodiment of the invention, the support can for example comprise both the working electrode and the counter electrode even before the paste is applied. Alternatively, however, it is equally possible to apply the working electrode and the counter electrode to the support only once the paste has been applied and hardened. The manufacturing method according to the invention has proven advantageous in this respect, as both the paste and the electrodes can be applied to the support by means of screen printing and thus in a thin and defined layer thickness.

Typically, the method according to the invention further comprises introducing a liquid containing non-volatile electrolyte constituents, for example a liquid electrolyte, into the porous, non-swellable framework structure and subsequently evaporating the volatile constituents thereof. From these non-volatile constituents, it is possible to form the liquid electrolyte which ensures the electrically conductive connection between the working electrode and the counter electrode in the sensor according to the invention. The liquid can in this case be introduced into the pores of the non-swellable framework structure using processes such as have been described in relation to the account of the electrochemical sensor.

Alternatively, it is possible to introduce, even before the formation of the porous, non-swellable framework structure, a liquid containing the non-volatile electrolyte constituents into a mixture containing at least one particulate material with at least one binder and, if appropriate, further substances, as a result of which it is possible to achieve in a simple manner a uniform distribution of the solid constituents of the electrolyte in the porous, non-swellable framework structure which is obtained after hardening of the mixture. In a typical embodiment of the invention, the method according to the invention includes introducing the liquid into a paste, it being possible to add the liquid to the paste in particular before the paste is applied to a suitable support. This embodiment involves adding a liquid containing the non-volatile electrolyte constituents typically in a solvent which is miscible with the binder. This solvent may for example be a glycol, for example ethylene glycol, propylene glycol or a mixture thereof, which can if appropriate contain up to 20% (v/v) of water.

In another typical embodiment, putting the electrochemical sensor according to the invention into operation further includes the prior activation thereof using suitable means. The activation can be caused, for example, by bringing the sensor into contact with a suitable liquid, in particular with an aqueous liquid. During the process, the liquid serving to activate the sensor, in particular water, passes, for example as a result of isothermal distillation, through the gas-permeable cover layer of the electrochemical sensor and condenses in the pores of the non-swellable framework structure, the previously introduced solid constituents of the electrolyte liquid being dissolved.

Typical liquids for activating the sensor have an osmotic pressure which corresponds or is similar to the osmotic pressure of the electrolyte liquid absorbed in the porous, non-swellable framework structure of the sensor, and comprise in particular aqueous calibration and control liquids, for example buffer systems or saline solutions having a salt concentration of from about 100 to about 200 mmol/l, or osmolarity values of from about 200 mosmol/l to about 500 mosmol/l. If the analyte to be determined is contained in an aqueous liquid, then the sensor can, if appropriate, also be activated by means of the aqueous measuring medium.

A long storage life and a long in-use service life of the electrochemical sensor can be ensured using this method. Alternatively, however, the present invention also provides for the electrolyte layer to contain the electrolyte already in liquid form before the electrochemical sensor is put into operation.

For determining the gaseous analyte, the electrochemical sensor according to the invention can be configured in any desired manner which allows a contact between the electrochemical sensor and the aqueous measuring medium. Thus, the sensor can, for example, be embodied as a measuring cell through which the aqueous measuring medium containing the gaseous analyte is passed. Furthermore, the sensor according to the invention can be embodied together with further sensors, which serve, for example, to determine different point-of-care parameters, in exchangeable measuring chambers (sensor cartridges).

Depending on the presence and/or the amount of the analyte, the sensor generates a measurable signal. Typically, this signal is an electrical signal, for example electric current, voltage, resistance, etc., which is evaluated or read using suitable means. Typically, the electrochemical sensor is an amperometric sensor, for example in the case of an oxygen sensor, or a potentiometric sensor, for example in the case of a carbon dioxide sensor.

In order that the invention may be more readily understood, reference is made to the following examples, which are intended to illustrate the invention, but not limit the scope thereof.

EXAMPLES

Example 1

Production of a Screen-Printable Paste 12.0 g of ethyl cellulose powder N 50 and 192.0 g of terpineol were weighed into a closable glass and the mixture was stirred for 2 weeks at room temperature until the ethyl cellulose had completely dissolved. In order to produce an amount of 100 g of ready-to-use, screen-printable paste, 25.6 g of the ethyl cellulose solution obtained, 32.3 g of phenolic resin PR 373, 1.0 g of the antifoaming agent Byk 051 (from Byk Chemie), 5.0 g of benzyl alcohol and 2.9 g of butyl diglycol were subsequently weighed into a beaker glass and this mixture was intensively stirred. 43.2 g of the zeolite LZ-Y 52 (from Sigma-Aldrich, product no. 334448) were added to this mixture and the mixture was intensively stirred until the filler was distributed homogeneously to obtain a screen-printable paste.

Example 2

Determining the Relative Absorption of Liquid of a Paste which is Produced and Hardened in Accordance with Example 1

In order to determine the relative absorption of liquid of a paste produced in accordance with Example 1, a plurality of slides (76×26 mm, ISO Standard 8038/I, from Roth) were weighed out on an analytical balance ($m_{support}$). Test layers were subsequently applied to the slides by applying the paste produced in accordance with Example 1 to the slides using an 80 μm helical stripping doctor blade. The applied paste covered a rectangular area of about 60×18 mm. As this area is variable, it was determined exactly only once the paste had hardened. 10-15 minutes after the application of the paste, the test pieces were hardened in a drying cabinet for 4 h at 110° C. Subsequently, the test pieces were stored in a desiccator (over CaO) until measurement. The slides with the hardened paste were reweighed ($m_{dry}$) and immediately thereafter immersed in each case into about 40 ml of liquid which was located in screwable plastic boxes having a volume of 100 ml. The boxes with the immersed test pieces remained closed while the measuring was carried out. At defined points in time, the test pieces were removed from the boxes, dabbed off and weighed in order to determine the amount of absorbed liquid. The measurements were terminated when the amount of absorbed liquid, and thus the mass ($m_{wet}$), remained constant. The measurements were carried out at room temperature and normal pressure. From the measured values collected, the relative absorption of liquid for each test piece was calculated as the mean value of the corresponding measured values of at least 3 test pieces, with a standard deviation of at most 1%.

The respective relative absorption of liquid was correlated in each case to the previously determined dry weight of the hardened paste (in each case less the weight of the slide): (relative absorption of liquid [%]=[($m_{wet}$−$m_{support}$)/($m_{dry}$−$m_{support}$)−1]*100). The values of the relative absorption of liquid change in accordance with the porosity of the hardened paste. Hardened pastes having undesirably high porosity have relative absorptions of liquid of between 50% and 70%; hardened pastes having undesirably low porosity have relative absorptions of liquid of less than 20%. Hardened pastes which are used within the present invention have a porosity which causes a relative absorption of liquid of between 20% by weight and 50% by weight, typically between 26% by weight and 44% by weight.

Example 3

Production of a Sensor Semifinished Product with a Porous Electrolyte Layer

In order to produce a sensor semifinished product which can be used as a component of an electrochemical sensor according to the present invention, the paste produced in accordance with Example 1 was applied to a screen, applied to a suitable support, comprising a working electrode and a counter electrode, by means of screen printing and hardened at elevated temperature. The thickness of the hardened layer was 10-20 µm.

Example 4

Introduction of an Electrolyte which is Suitable for $O_2$ Sensors into the Pores of the Sensor Semifinished Product Produced in Accordance with Example 3

In order to produce 100 g of inner electrolyte for an electrochemical $O_2$ sensor according to the present invention, 0.098 g of $Na_2HPO_4$ (p.a.), 0.094 g of $KH_2PO_4$ (p.a.), 0.257 g of NaCl (p.a.), 0.060 g of polyethylene glycol 6000 (for synthesis) and 0.744 g of glycerol (p.a.) were dissolved in 98.75 g of deionised water, a pH-buffered electrolyte solution being obtained. The salts were introduced into the porous electrolyte layer by means of an excess method. For this purpose, before the electrolyte solution was introduced, the sensor semifinished product produced in accordance with Example 3 was firstly stored for 1 h in a vessel over deionised water at 100% relative humidity of air. Subsequently, the excess electrolyte solution was dispensed onto the upwardly open, porous layer of the sensor and the excess was removed using a filter paper. In a closed vessel, the sensor semifinished product treated in this way was subsequently stored over water at 100% relative humidity of air until the pores of the porous layer had been filled with the electrolyte solution (approx. 2 h). After removal of the electrolyte solution supernatant using a filter paper, the sensor semifinished product was stored for 72 h at 65° C. for the purposes of evaporating the volatile constituents.

Example 5

Introduction of an Electrolyte which is Suitable for $CO_2$ Sensors into the Pores of the Sensor Semifinished Product Produced in Accordance with Example 3

In order to produce 100 g of inner electrolyte solution for an electrochemical $CO_2$ sensor according to the present invention, 0.252 g of $NaHCO_3$ (p.a.) and 0.559 g of KCl (p.a.) were dissolved together with 0.15 g of the enzyme carbonic anhydrase (from Serva, product no. 15880) in 99.04 g of deionised water. As in Example 4, the electrolyte solution was introduced into the porous layer produced in accordance with Example 3 by means of an excess method.

Example 6

Production of a Sensor Semifinished Product which is Suitable for $O_2$ Sensors and has a Porous Electrolyte Layer

An alternative embodiment to Examples 3 and 4 includes already introducing into the screen-printable paste the non-volatile electrolyte constituents in a suitable solvent.

In order to produce a sensor semifinished product which can be used as a component of an electrochemical $O_2$ sensor according to the present invention, 0.120 g of $Na_2HPO_4$ (p.a.), 0.110 g of $KH_2PO_4$ (p.a.), 0.310 g of NaCl (p.a.) and 0.066 g of polyethylene glycol 6000 (for synthesis) were dissolved in 1.6 g of deionised water. The solution obtained in this way was subsequently mixed with a solution of 0.900 g of glycerol (p.a.) in 23.15 g of ethylene glycol and stirred until a clear solution was obtained.

In order to produce the sensor semifinished product, 4.2 g of the aqueous ethylene glycol solution were stirred into 100 g of the paste produced in accordance with Example 1, whereupon the paste containing the liquid electrolyte was applied to a suitable support by means of screen printing and hardened at elevated temperature. A subsequent dispensing step is not required.

Example 7

Production of a Sensor Semifinished Product which is Suitable for $CO_2$ Sensors and has a Porous Electrolyte Layer

An alternative embodiment to Examples 3 and 5 includes already introducing into the screen-printable paste the non-volatile electrolyte constituents in a suitable solvent.

In order to produce a sensor semifinished product which can be used as a component of an electrochemical $CO_2$ sensor according to the present invention, 0.150 g of $Na_2CO_3$ (p.a.) and 0.250 g of KCl (p.a.) were dissolved in 1.6 g of deionised water. This solution was then mixed with 8 g of ethylene glycol and stirred until a clear solution was obtained.

In order to produce the sensor semifinished product, 2.69 g of the aqueous ethylene glycol solution were stirred into 100 g of the paste produced in accordance with Example 1, whereupon the paste containing the liquid electrolyte was applied to a suitable support by means of screen printing and hardened at elevated temperature. A subsequent dispensing step is not required.

Example 8

Application of a Gas-Permeable Cover Layer to the Sensor Semifinished Product Produced in Accordance with One of Examples 4-7 and Packaging of the Ready-to-Use Sensor Plates

A cover layer was applied by means of screen printing to the sensor semifinished product produced in accordance with one of Examples 4-7. For this purpose, an oxime-cleaving silicone was applied to the sensor semifinished product by means of screen printing and hardened at elevated temperature. The thickness of the hardened layer was approx. 10 µm. The sensor plates obtained in this way were subsequently packaged in an airtight manner in a suitable container for the purposes of storage until use.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined by the appended claims. More specifically, although some aspects of the present invention are identified herein as preferred or particularly advantageous, it is contemplated that the present invention is not necessarily limited to these preferred aspects of the invention.

What is claimed is:

1. An electrochemical sensor for determining a gaseous analyte dissolved in an aqueous measuring medium, comprising:
   (a) a working electrode and a counter electrode,
   (b) an electrolyte layer located between the working electrode and the counter electrode, and
   (c) a gas-permeable cover layer configured to spatially separate the working electrode, the counter electrode and the electrolyte layer from the aqueous measuring medium, wherein the electrolyte layer comprises at least one particulate material and at least one binder which together form a porous, non-swellable framework structure, the pores of the non-swellable framework structure configured to absorb a liquid electrolyte or contain the liquid electrolyte.

2. The electrochemical sensor according to claim 1, wherein the particulate material is an inorganic particulate material selected from the group consisting of controlled porous glass (CPG), silica gels, silicates and alumosilicates.

3. The electrochemical sensor according to claim 1, wherein the particulate material is a naturally occurring or synthetic alumosilicate.

4. The electrochemical sensor according to claim 1, wherein the particulate material has channels, said channels having a diameter of between about 0.1 nm and about 10 nm.

5. The electrochemical sensor according to claim 4, wherein said channels further comprise ion exchanger groups.

6. The electrochemical sensor according to claim 1, wherein the particulate material is zeolite.

7. The electrochemical sensor according to claim 1, wherein the particulate material is faujasite.

8. The electrochemical sensor according to claim 1, wherein the particles of the particulate material have an average particle diameter of from about 0.1 μm to about 10 μm.

9. The electrochemical sensor according to claim 1, wherein the particles of the particulate materials have an average particle diameter of from about 1.0 μm to about 5.0 μm.

10. The electrochemical sensor according to claim 1, wherein the binder is an organic binder.

11. The electrochemical sensor according to claim 10, wherein the organic binder comprises a crosslinked or uncrosslinked synthetic polymer.

12. The electrochemical sensor according to claim 11, wherein the crosslinked or uncrosslinked synthetic polymer is a compound selected from the group consisting of a phenolic resin, an epoxy resin, a vinyl resin, a PVC copolymer, a two-component epoxy resin, a polyurethane resin system and a UV-curable polyacrylate monomer mixture.

13. The electrochemical sensor according to claim 12, wherein the UV-curable polyacrylate monomer mixture is a phenolic resin.

14. The electrochemical sensor according to claim 1, wherein the pores of the non-swellable framework structure have a diameter of from about 500 nm to about 5 μm.

15. The electrochemical sensor according to claim 1, wherein the pores of the non-swellable framework structure have a diameter of from about 1 μm to about 3 μm.

16. The electrochemical sensor according to claim 1, wherein the porous, non-swellable framework structure causes a relative absorption of liquid of from about 20% by weight to about 50% by weight based on the dry weight of the porous, non-swellable framework structure.

17. The electrochemical sensor according to claim 1, wherein the porous, non-swellable framework structure causes a relative absorption of liquid of from about 26% by weight to about 44% by weight based on the dry weight of the porous, non-swellable framework structure.

18. The electrochemical sensor according to claim 1, wherein the electrolyte layer has a thickness of from about 5 μm to about 30 μm.

19. The electrochemical sensor according to claim 1, wherein the electrolyte layer has a thickness of from about 10 μm to about 20 μm.

20. The electrochemical sensor according to claim 1, wherein the liquid electrolyte comprises an alkali metal chloride and a pH buffer system.

21. The electrochemical sensor according to claim 20, wherein the liquid electrolyte further comprises a water-soluble polymer.

22. The electrochemical sensor according to claim 21, wherein the water-soluble polymer is polyethylene glycol and/or polyvinylpyrrolidone.

23. The electrochemical sensor according to claim 20, wherein the liquid electrolyte further comprises an enzyme.

24. The electrochemical sensor according to claim 23, wherein the enzyme is carbonic anhydrase.

25. The electrochemical sensor according to claim 1, wherein the electrolyte layer comprises the non-volatile constituents of the liquid electrolyte before the sensor is put into operation.

26. The electrochemical sensor according to claim 1, wherein the gas-permeable cover layer is impermeable to ions and non-volatile constituents of the aqueous measuring medium.

27. The electrochemical sensor according to claim 1, wherein the gas-permeable cover layer comprises a siloxane, a polysulphone and/or polytetrafluoroethylene.

28. The electrochemical sensor according to claim 1, wherein the gas-permeable cover layer has a thickness of from about 5.0 μm to about 30 μm.

29. The electrochemical sensor according to claim 1, wherein the gas-permeable cover layer has a thickness of from about 8.0 μm to about 15 μm.

30. The electrochemical sensor according to claim 1, wherein the working electrode is made of a gold or ruthenium oxide-based composite material.

31. The electrochemical sensor according to claim 1, wherein the counter electrode is made of a silver or silver/silver chloride-based composite material.

32. The electrochemical sensor according to claim 1, wherein the sensor is configured for a multiple determination of the gaseous analyte dissolved in the aqueous measuring medium.

33. The electrochemical sensor according to claim 1, wherein the sensor is configured for determining a gaseous analyte in a body fluid.

34. The electrochemical sensor according to claim 33, wherein the body fluid is whole blood, plasma or serum.

35. The electrochemical sensor according to claim 1, wherein the gaseous analyte is oxygen.

36. The electrochemical sensor according to claim 1, wherein the gaseous analyte is carbon dioxide.

37. A method for manufacturing an electrochemical sensor according to claim 1, comprising:
   (a) providing at least one particulate material;
   (b) mixing the particulate material with at least one binder;
   (c) processing the mixture obtained in step (b) into a paste;
   (d) applying the paste obtained in step (c) to a support;
   (e) hardening the paste applied to the support to form a porous, non-swellable framework structure; and (f) producing an electrochemical sensor containing the porous, non-swellable framework structure obtained in step (e) as an electrolyte layer, and also a working electrode, a counter electrode and a gas-permeable cover layer.

38. The method according to claim 37 further comprising introducing a liquid containing non-volatile electrolyte constituents into the porous, non-swellable framework structure and subsequently evaporating the volatile constituents of the liquid.

39. The method according to claim 37 further comprising introducing a liquid containing non-volatile electrolyte constituents into the paste obtained in step (c).

40. The method according to claim 37 further comprising activating the electrochemical sensor by contacting said sensor with a liquid.

41. The method according to claim 40, wherein said liquid is an aqueous liquid.

42. The method according to claim 40, wherein the liquid has an osmotic pressure corresponding to the osmotic pressure of the liquid electrolyte absorbed in the porous, non-swellable framework structure.

43. A method for determining a gaseous analyte dissolved in an aqueous measuring medium, comprising:
   (a) contacting the aqueous measuring medium with an electrochemical sensor according to claim 1, and
   (b) determining the gaseous analyte dissolved in the aqueous measuring medium by measuring a signal generated by the electrochemical sensor.

* * * * *